US008859837B2

(12) United States Patent
Mamedov et al.

(10) Patent No.: US 8,859,837 B2
(45) Date of Patent: Oct. 14, 2014

(54) PROCESS FOR OXIDATIVE DEHYDROGENATION OF PARAFFINIC LOWER HYDROCARBONS

(75) Inventors: Aggadin Kh. Mamedov, Sugar Land, TX (US); Ali S. Al-Khuraimi, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 271 days.

(21) Appl. No.: 13/130,706

(22) PCT Filed: Nov. 23, 2009

(86) PCT No.: PCT/EP2009/008295
§ 371 (c)(1),
(2), (4) Date: Dec. 15, 2011

(87) PCT Pub. No.: WO2010/057663
PCT Pub. Date: May 27, 2010

(65) Prior Publication Data
US 2012/0088947 A1    Apr. 12, 2012

(30) Foreign Application Priority Data
Nov. 24, 2008    (EP) .................................... 08020385

(51) Int. Cl.
*C07C 5/333*    (2006.01)
*C01B 3/34*    (2006.01)

(52) U.S. Cl.
CPC ...... *C07C 5/3335* (2013.01); *C10G 2300/4018* (2013.01); *C10G 2300/1081* (2013.01); *C07C 2523/34* (2013.01); *C10G 2400/20* (2013.01); *C01B 3/34* (2013.01)
USPC ............ 585/638; 585/639; 585/661; 585/663

(58) Field of Classification Search
USPC ......... 585/658, 654, 656, 659, 661–663, 900; 502/302, 303, 241
See application file for complete search history.

(56) References Cited

U.S. PATENT DOCUMENTS

| 3,763,255 A | 10/1973 | Hayes |
| 2002/0173420 A1* | 11/2002 | Cantrell et al. ................ 502/150 |
| 2004/0010174 A1 | 1/2004 | Wang et al. |
| 2004/0181107 A1 | 9/2004 | Abdulwahed et al. |
| 2007/0100190 A1* | 5/2007 | Cimino et al. ................ 585/658 |

FOREIGN PATENT DOCUMENTS

| EP | 1166869 A1 | 1/2002 |
| RU | 2035444 C1 | 5/1995 |

OTHER PUBLICATIONS

Krylov et al. Catalysis Today 24 (1995) 371-375.*
Wang et al. Energy and Fuels (2004) 18; 1126-1139.*
Grabowski et al.; "Oxidative Dehydrogenation of Isobutane on Supported Chromia Catalysts", Applied Catalysis A: General, vol. 144; 1996; pp. 335-341.
Krylov et al.; "Heterogeneous Catalytic Reactions of Carbon Dioxide"; Russian Chemical Review, vol. 64, Issue 9; 1995; pp. 877-900.
International Search Report; International Application No. PCT/EP2009/008295; International Filing Date: Nov. 23, 2009; 3 Pages.
Written Opinion of the International Searching Authority; International Application No. PCT/EP2009/008295; International Filing Date: Nov. 23, 2009; 5 Pages.
Sun et al.; "Kinetics of the Oxidative Dehydrogenation of Isobutane over Cr2O3/La2(CO3)3"; Journal of Natural Gas Chemistry, vol. 11; 2002; pp. 70-78.

* cited by examiner

*Primary Examiner* — In Suk Bullock
*Assistant Examiner* — Sharon Pregler
(74) *Attorney, Agent, or Firm* — Cantor Colburn LLP

(57) ABSTRACT

The present invention relates to a process for producing lower olefinic hydrocarbons by oxidative dehydrogenation of paraffinic lower hydrocarbons. More particularly the present invention provides a process for converting a feedstream comprising a paraffinic lower hydrocarbon and carbon dioxide to a product stream comprising an olefinic lower hydrocarbon and synthesis gas in the presence of the catalyst composition La—Mn/inert support, wherein said catalyst composition comprises 1-10 mass % lanthanum and 1-10 mass % manganese and optionally 0.3-3 mass % alkali metal.

17 Claims, No Drawings

PROCESS FOR OXIDATIVE DEHYDROGENATION OF PARAFFINIC LOWER HYDROCARBONS

CROSS REFERENCE TO RELATED APPLICATIONS

This application is a 371 of International Application No. PCT/EP2009/008295, filed Nov. 23, 2009, which claims priority to European Application No. 08020385.4, filed Nov. 24, 2008, both of which are hereby incorporated by reference in its entirety.

TECHNICAL FIELD

The present invention relates to a process for converting a feedstream comprising a paraffinic lower hydrocarbon and carbon dioxide to a product stream comprising an olefinic lower hydrocarbon and synthesis gas.

BACKGROUND ART

Olefinic lower hydrocarbons such as propene, butenes and isobutene are very important intermediates in the petrochemical industry. Such olefins are primarily produced as co-products in catalytic and steam cracking processes. Alternatively, lower olefins can be commercially produced by catalytic dehydrogenation of the corresponding lower alkanes. U.S. Pat. No. 3,763,255 for instance describes a method for dehydrogenation of C4-C30 hydrocarbons using a catalyst which comprises a platinum component, an iridium component and an alkali or alkaline earth metal component with a porous carrier material. The applicability of conventional endothermic dehydrogenation of lower alkanes, however, is limited by thermodynamic constraints and rapid catalyst deactivation caused by coke formation.

Oxidative dehydrogenation (ODH) of lower alkanes is a potentially advantageous alternative due to the exothermic nature of the overall reaction. Different supported and unsupported catalyst compositions useful in the oxidative dehydrogenation of C3-C5 hydrocarbons in general and of isobutane in particular have been described. A critical aspect of such catalyst compositions is the selectivity for the produced olefin (e.g. isobutene), since the formation of carbon oxides is thermodynamically much more favourable than the formation of olefin.

U.S. 2004/0010174 A describes a process for ODH of hydrocarbon feedstocks having from 2 to 10 carbon atoms characterized in that a circulating fluidized bed/regenerator system is employed. Accordingly, a mixed metal oxide catalyst is reduced in the ODH reactor and the reduced catalyst is transported to a separate regenerator system for reoxidation with air. The catalyst employed in the process according to U.S. 2004/0010174 A has the general formula $\alpha AO_x$-$\beta BO_y$-$\gamma CO_z$, wherein A is a precious metal and/or transition metal; B is a rare earth metal; C is an element chosen from Groups IIA, IIIA and IVA; and O is oxygen. $\alpha$, $\beta$ and $\gamma$ are the relative molar ratios of each metal oxide. U.S. 2004/0010174 A remains silent with respect to the selectivity and the yield of the disclosed process.

In EP 1166869 A a method for ODH of hydrocarbons is described comprising contacting a hydrocarbon with a tungsten-based catalyst composition in the presence of molecular oxygen at 350° C. to 550° C. The tungsten-based catalyst composition of EP 1166869 A has the general formula $X_xY_y$-$WO_z$, wherein X is at least one element selected from the group consisting of Li, Na, K, Rb, Cs and Fr; Y is at least one element selected from the group consisting of B, Al, Ga, In, Ti, C, Si, Ge, Sn and Pb; W is tungsten; and O is oxygen and wherein x is 0.5-2.5, y is 0.05-5, and z is the number to satisfy the valency of X, Y and W. When using the catalyst composition $Na_2SiWO_x$ as catalyst at a reaction temperature of 500° C., an isobutene selectivity of 70.0 and an isobutene yield of 8.2 could be achieved.

Supported chromium-based catalyst compositions that are commercially used in endothermic catalytic dehydrogenation of lower alkanes may also be used in oxidative dehydrogenation (ODH) processes.

In GRABOWSKI, et al., Oxidative dehydrogenation of isobutane on supported chromia catalysts, *Applied Catalysis*. 1996, vol. 144, p. 335-341, for instance, the use of chromia supported on silica ($CrO_x/SiO_2$), alumina ($CrO_x/Al_2O_3$), titania ($CrO_x/TiO_2$), zirconia ($CrO_x/ZrO_2$) and magnesia ($CrO_x/MgO$) as a catalyst for ODH of isobutane in the presence of molecular oxygen is described. The highest isobutene selectivity (70% at 5% conversion) and isobutene yield (9%) could be obtained by using $CrO_x/TiO_2$ and K-promoted $CrO_x/Al_2O_3$ catalyst compositions.

SUN, et al., Kinetics of the oxidative dehydrogenation of isobutane over Cr2O3/La2(Co3)3, *J Nat Gas Chem.* 2002, vol. 11, p. 70-78 describes the use of chromia supported on lanthanum carbonate ($Cr_2O_3/La_2(CO_3)_3$) as a catalyst for ODH of isobutane in the presence of molecular oxygen. By using said $Cr_2O_3/La_2(CO_3)_3$ catalyst, an isobutene selectivity of 95% and 12.5% conversion at a reaction temperature of 230-250° C. can be achieved.

Besides by selecting the catalyst composition, the selectivity and/or yield of a process for ODH of a lower alkane can be influenced by the composition of the feedstream. As described in SUN, et al, Kinetics of the oxidative dehydrogenation of isobutane over Cr2O3/La2(Co3)3, *J Nat Gas Chem.* 2002, vol. 11, p. 70-78 for instance, ODH of isobutane to isobutene over Cr—Mn—O/$Al_2O_3$ is three times greater in the presence of carbon dioxide in the reaction mixture. More particularly, KRYLOV, et al, Heterogeneous catalytic reaction of carbon dioxide, *Russian Chemical Reviews* 1995, vol. 64, p. 877-900 describes that in the presence of a Cr—Mn—O/$Al_2O_3$ catalyst isobutane conversion reaches 61-66% at an isobutene selectivity of 78-81%. Equal amounts of carbon monoxide and hydrogen are further produced in said ODH reaction.

In RU 2035444 C a process for conversion of isobutane to isobutene in the presence of carbon dioxide at 610-680° C. is disclosed, wherein the molar ratio of isobutane to carbon dioxide in the feed is 0.8-1.4:1. The employed catalyst contains 2-6 mass % Cr and 2-6 mass % Mn supported on $\gamma$-$Al_2O_3$.

Also in U.S. 2004/0181107 a process for alkane dehydrogenation is disclosed which comprises contacting an alkane with a chromium-based dehydrogenation catalyst in the presence of carbon dioxide. The molar ratio of alkane and carbon dioxide is about 1:0.0001 to 1:0.045.

Although reasonable isobutene yields can be obtained by employing chromium-based dehydrogenation catalysts, catalyst performance is not stable due to coke formation and decreases within several hours. As a further disadvantage, chromium-based catalysts are environmentally problematic due to the high toxicity of many chromium compounds.

The technical problem underlying the present invention is the provision of a process for oxidative dehydrogenation (ODH) of lower alkanes having a high selectivity and yield of the produced olefin and wherein the used catalyst has an improved stability against deactivation and is less environmentally problematic when compared to chromium-based catalysts.

Disclosure of Invention

The solution to the above problem is achieved by providing the process characterized by the claims and as described herein below.

Accordingly, the present invention provides a process for converting a feedstream comprising a paraffinic lower hydrocarbon and carbon dioxide to a product stream comprising an olefinic lower hydrocarbon and synthesis gas, said process comprising a step of contacting the feedstream with a catalyst composition "La—Mn/inert support", wherein said catalyst composition comprises 1-10 mass % La (lanthanum) and 1-10 mass % Mn (manganese).

In the context of the present invention, it was surprisingly found that by using a catalyst composition "La—Mn/inert support" as defined herein, stable catalyst performance over 4 hours could be achieved in a process wherein the paraffinic lower hydrocarbon isobutane (i-$C_4H_{10}$) is converted to the olefinic lower hydrocarbon isobutene (i-$C_4H_8$) in the presence of carbon dioxide ($CO_2$). When applying a conventional $Cr/Al_2O_3$-based catalyst or Manganese-modified $Cr/Al_2O_3$-catalyst under comparable process conditions, catalyst performance decreases within two hours. In addition to the improved catalyst stability, the selectivity and yield of the produced olefinic lower hydrocarbon (e.g. isobutene) is improved in the process of the present invention.

As used herein, the terms "paraffinic lower hydrocarbon" or "lower alkane" relates to a saturated hydrocarbon having the general formula $C_nH_{2n+2}$ and having from 2 to 8 carbon molecules. Preferably, the "paraffinic lower hydrocarbon" that is comprised in the feedstream of the process of the present invention comprises from 3 to 5 carbon molecules. The term "olefinic lower hydrocarbon" or "lower alkene" as used in the context of the present invention relates to an unsaturated hydrocarbon having the general formula $C_nC_{2n}$ and having from 2 to 8 carbon molecules. Accordingly, an "olefinic lower hydrocarbon" as used herein comprises one carbon-to-carbon double bond. Preferably, the "olefinic lower hydrocarbon" comprises from 3 to 5 carbon molecules.

Although the feedstream of the process of the present invention may comprise a mixture of different lower alkane species (such as, but not limited to, n-butane and isobutane) it is preferred that said feedstream predominantly comprises only one lower alkane species. Accordingly, it is preferred that the lower alkane comprised in the feedstream consists of at least 75 mole % of only one lower alkane species, more preferably of at least 85 mole % of only one lower alkane species, even more preferably of at least 90 mole % of only one lower alkane species, particularly preferably of at least 95 mole % of only one lower alkane species and most preferably of at least 98 mole % of only one lower alkane species.

The paraffinic lower hydrocarbon that is most preferably used in the process of the present invention is isobutane. The lower alkene that is accordingly produced by the ODH of isobutane is isobutene. Further components of the product stream produced by ODH of isobutane include, but are not limited to, carbon dioxide, isobutene, propane and synthesis gas.

It is an advantage of the process of the present invention that as a by-product synthesis gas (syngas) is formed having a (nearly) stoichiometric $H_2/CO$ ratio of approximately 1 (0.8-1.2). Syngas having stoichiometric composition is particularly useful in carbonylation reactions, e.g. for producing dimethyl ether (DME). In one aspect of the present invention accordingly, the syngas as comprised in the product stream of the process of the present invention is separated from the remaining components of the product stream and is used as a feedstream in a further process, such as a Fisher-Tropsch synthesis process, a methanol synthesis process, a dimethyl ether synthesis process, an acetic acid synthesis process or an ammonia synthesis process. Preferably, the syngas is used as a feed in a carbonylation reaction (e.g. for producing dimethyl ether or methanol).

The "La—Mn/inert support" catalyst composition of the present invention comprises at least 1 mass % lanthanum but not more than 10 mass % lanthanum (1-10 mass % La) and at least 1 mass % manganese but not more than 10 mass % manganese (1-10 mass % Mn). Preferably, the catalyst composition employed in the process of the present invention comprises at least 2 mass % La, more preferably at least 2.5 mass % La and even more preferably at least 3 mass % La. Furthermore, the catalyst composition employed in the process of the present invention preferably comprises not more than 8 mass % La, more preferably not more than 6 mass % La and even more preferably not more than 5 mass % La. Most preferably, the catalyst composition of the present invention comprises about 4 mass % La. Moreover, the catalyst composition employed in the process of the present invention preferably comprises at least 2 mass % Mn, more preferably at least 2.5 mass % Mn and even more preferably at least 3 mass % Mn. Furthermore, the catalyst composition employed in the process of the present invention preferably comprises not more than 8 mass % Mn, more preferably not more than 6 mass % Mn and even more preferably not more than 5 mass % Mn. Most preferably, the catalyst composition of the present invention comprises about 4 mass % Mn.

Any conventional inert support or inert carrier that is stable under the relevant process conditions may be used in the catalyst composition "La—Mn/inert support" as defined herein. Preferably, the inert support as comprised in the catalyst composition "La—Mn/inert support" is selected from the group consisting of alumina ($Al_2O_3$), silica ($SiO_2$), titania ($TiO_2$) and zirconia ($ZrO_2$) and magnesia (MgO) and mixtures thereof. More preferably, the inert support is $Al_2O_3$ and most preferably the inert support is $\gamma$-$Al_2O_3$ The catalyst composition of the present invention may further comprise at least 0.3 mass % but not more than 3 mass % (0.3-3 mass %) alkali metal (Group 1; IUPAC Periodic Table of the Elements, 2007) as a promoter. Preferably, the catalyst composition comprises at least 0.5 mass % alkali metal, more preferably at least 0.7 mass % alkali metal, even more preferably at least 1 mass % alkali metal. Furthermore, the catalyst composition preferably comprises not more than 2.5 mass % alkali metal, more preferably not more than 2 mass % alkali metal, even more preferably not more than 1.8 mass % alkali metal. Most preferably, the catalyst composition of the present invention comprises 1.5 mass % alkali metal (Group 1) as a promoter. Preferably, said alkali metal is selected from the group consisting of Li (lithium), Na (sodium), and K (potassium). Most preferably, the catalyst composition of the present invention comprises the promoter K (potassium).

The "La—Mn/inert support" catalyst composition used in the process of the present invention may be manufactured by any conventional method known in the art. In one embodiment, the inert support is impregnated with a solution comprising La and Mn salts and, optionally, alkali metal salts. Said La salt used when manufacturing the catalyst composition may be $La(NO_3)_3$, said Mn salt may be $Mn(CH_3COO)_2$ and/or said alkali metal salt may be KOH. The resulting composition may be dried (e.g. for 12 hours at 120° C.). The impregnated support then is calcined in the presence of oxygen (e.g. for 2 hours at 500° C. in air) and reduced using a conventional reducing agent known in the art (e.g. for 3 hours using $H_2$ as reducing agent).

The reaction temperature of the process of the present invention preferably is at least 550° C., more preferably at least 600° C. and most preferably at least 670° C., but preferably not higher than 710° C., more preferably not higher than 700° C. and most preferably not higher than 690° C. If the reaction temperature becomes too high (e.g. higher than 710° C.) unwanted side-reactions may be promoted. The reaction pressure of the process of the present invention is not particularly critical and can vary from atmospheric to 0.5 MPa, however a reaction pressure of not more than 0.2 MPa is preferred. The space velocity of the process of the present invention is about 400-600 $h^{-1}$. The isobutane to $CO_2$ ratio is about 0.7-1.

The process of the present invention may be operated in a fixed bed reactor or slow moving bed reactor. However, due to the space velocity applicable for this reaction the fixed bed reactor is preferred.

MODE(S) FOR CARRYING OUT THE INVENTION

The present invention will now be more fully described by the following non-limiting Examples.

Example 1 (Comparative)

A plug flow quartz reactor with an inner diameter of 12 mm was filled with 12 ml industrial Catofin® catalyst (Sud-Chemie; fixed bed Cr/alumina catalyst) and a reaction mixture consisting of 43.8% $i-C_4H_{10}$+48.9% $CO_2$+7.3% $N_2$ was passed over the catalyst bed at a flow rate of 80 cc/min.

The term "isobutane conversion" or "$i-C_4H_{10}$ conv." as used herein is defined as: [[(Moles $i-C_4H_{10}$ in feed)−(Moles $i-C_4H_{10}$ in effluent)]/(Moles $i-C_4H_{10}$ in feed)]×100.

The term "isobutene selectivity" or "$i-C_4H_8$ sel." as used herein is defined as: [(Moles $i-C_4H_8$ in effluent)/(Moles $i-C_4H_{10}$ conv.)]×100.

The term "propene selectivity" or "$C_3H_6$ sel." as used herein is defined as: [(Moles $i-C_3H_6$ in effluent)/(Moles $i-C_4H_{10}$ conv.)]×100.

The term "isobutene yield" or "$i-C_4H_8$ yield." as used herein is defined as: [(Moles $i-C_4H_8$ formed)/(Moles $i-C_4H_{10}$ in feed)]×100.

The results obtained in Example 1 are described in Table 1 as provided herein below.

TABLE 1

| Temp (° C.) | Duration (min) | $iC_4H_{10}$ conv. (%) | $iC_4H_8$ sel. (%) | $C_3H_6$ sel. (%) | $iC_4H_8$ yield (%) | Total C3-C4 sel. (%) | Outlet concentration (mole %) | | | |
|---|---|---|---|---|---|---|---|---|---|---|
| | | | | | | | $iC_4H_8$ | $C_3H_6$ | CO | $H_2$ |
| 610 | 5 | 67.8 | 59.0 | 5.8 | 40.0 | 64.8 | 16.9 | 1.67 | 12.5 | 11.2 |
| 610 | 18 | 50.2 | 50.0 | 7.4 | 25.1 | 57.4 | 11.0 | 1.63 | 8.7 | 7.5 |
| 610 | 42 | 43.0 | 44.7 | 9.0 | 18.1 | 53.7 | 8.6 | 1.73 | 7.5 | 5.2 |
| After 30 min regeneration with air and 15 min reduction with $H_2$ | | | | | | | | | | |
| 670 | 5 | 92.2 | 48.3 | 18.7 | 44.5 | 67.0 | 16.9 | 6.6 | 19.3 | 15.4 |
| 670 | 15 | 68.8 | 54.8 | 20.6 | 37.7 | 75.4 | 14.9 | 6.4 | 14.4 | 11.0 |
| 670 | 45 | 45.3 | 59.3 | 16.5 | 26.8 | 75.8 | 10.2 | 4.7 | 9.2 | 8.0 |

Example 2 (Comparative)

Manganese-modified Cr/alumina Catofin® catalyst was prepared by impregnation of Catofin® catalyst with $Mn(CH_3COO)_2$, followed by a drying at 120° C. and calcination at 500° C. The resulting 4% Mn-Cr/$Al_2O_3$-. Catofin catalyst was contacted with a 43.8% $i-C_4H_{10}$+48.9% $CO_2$+ 7.3% $N_2$ reaction mixture at the same conditions as described in Example 1. The obtained results are described in the following Table 2.

TABLE 2

| Temp (°C.) | Duration (min) | iC$_4$H$_{10}$ conv. (%) | iC$_4$H$_8$ sel. (%) | C$_3$H$_6$ sel. (%) | iC$_4$H$_8$ yield (%) | Total C3-C4 sel. (%) | Outlet concentration (mole %) | | | |
|---|---|---|---|---|---|---|---|---|---|---|
| | | | | | | | iC$_4$H$_8$ | C$_3$H$_6$ | CO | H$_2$ |
| 670 | 10  | 40.3 | 27.4 | 28.8 | 11.0 | 56.4 | 4.39  | 4.6 | 12.6 | 10.5 |
| 670 | 40  | 45.7 | 51.9 | 18.4 | 23.7 | 70.3 | 9.38  | 3.3 | 13.1 | 11.0 |
| 670 | 65  | 50.8 | 68.2 | 16.4 | 34.6 | 84.6 | 14.2  | 3.4 | 9.4  | 7.6  |
| 670 | 85  | 48.1 | 68.1 | 17.4 | 32.7 | 85.5 | 14.2  | 3.4 | 8.4  | 6.5  |
| 670 | 125 | 48.7 | 68.2 | 16.4 | 33.2 | 84.6 | 14.2  | 3.4 | 7.7  | 5.6  |
| 670 | 170 | 45.4 | 70.6 | 18.1 | 32.1 | 88.7 | 13.9  | 3.4 | 7.2  | 5.0  |
| 690 | 185 | 61.7 | 68.2 | 18.9 | 42.1 | 87.1 | 16.9  | 4.7 | 9.6  | 7.0  |
| 690 | 200 | 56.9 | 69.0 | 18.7 | 39.2 | 87.7 | 16.0  | 4.3 | 8.8  | 6.3  |
| 690 | 220 | 56.8 | 68.6 | 18.9 | 38.9 | 87.5 | 15.8  | 4.4 | 8.5  | 6.2  |
| 690 | 245 | 53.8 | 70.1 | 19.1 | 37.7 | 89.2 | 15.4  | 4.2 | 8.2  | 6.0  |
| 690 | 270 | 53.2 | 72.2 | 20.1 | 38.4 | 92.3 | 15.4  | 4.3 | 8.1  | 6.0  |
| 690 | 290 | 52.1 | 70.1 | 19.7 | 36.5 | 89.7 | 14.9  | 4.2 | 7.7  | 5.7  |

Example 3

Catalyst composition 1.5% K-4% La-4% Mn/Al$_2$O$_3$ was prepared by impregnation of γ-Al$_2$O$_3$ with La(NO$_3$)$_3$, Mn(CH$_3$COO)$_2$ and KOH solutions. The resulting composition was dried at 120° C. for 12 hours, calcined for 2 hours at 500° C. in air and then reduced for 3 hours using H$_2$.

Oxidative dehydrogenation of isobutane in the presence of carbon dioxide has been carried out at the same conditions (at reaction temperature of 670° C.) as described in Examples 1 and 2 but with the difference that a non-chromium based composition 1.5% K-4% La-4% Mn/Al$_2$O$_3$ as described herein above was used as a catalyst. The results obtained with the 1.5% K-4% La-4% Mn/Al$_2$O$_3$ catalyst of the present invention are described in the following Table 3.

TABLE 3

| Time (min) | iC$_4$H$_{10}$ conv. (%) | iC$_4$H$_8$ sel. (%) | C$_3$H$_6$ sel. (%) | CO conc. (%) | H$_2$ conc. (%) | iC$_4$H$_8$ yield (%) | iC$_4$H$_8$ + C$_3$H$_6$ Yield (%) |
|---|---|---|---|---|---|---|---|
| 65  | 50.0 | 76.3 | 19.0 | 10.5 | 8.37 | 38.2 | 47.6 |
| 100 | 55.8 | 75.5 | 21.3 | 10.2 | 7.7  | 42.1 | 54.2 |
| 140 | 56.9 | 74.4 | 20.0 | 9.2  | 7.0  | 42.3 | 58.9 |
| 170 | 56.6 | 74.2 | 20.6 | 9.1  | 6.9  | 41.9 | 53.7 |
| 190 | 58.5 | 73.9 | 20.0 | 9.3  | 6.9  | 43.2 | 54.9 |
| 230 | 57.5 | 74.0 | 19.8 | 9.0  | 6.8  | 42.5 | 53.9 |

The feedstream consisted of 43.8 ml i-C4; 48.9 ml CO$_2$; and 7.2 ml N$_2$. The resulting product stream after 230 min. continuously running consisted of 19.2 ml i-C$_4$H$_8$; 18.1 ml i-C$_4$H$_{10}$; 7.2 ml N$_2$; 12.8 ml H$_2$; 14.8 ml CO; 36.1 ml CO$_2$; 5.4 ml C$_3$H$_6$; and 4.8 ml CH$_4$.

As can be seen from Example 3, the catalyst composition of the present invention shows no signs of deactivation over 4 hours while the conversion of i-C$_4$H$_{10}$ on a non-modified Cr/Al$_2$O$_3$-based Catofin catalyst shows a twofold decrease within 40 min; see Example 1. Manganese-modified Cr/Al$_2$O$_3$-Catofin catalyst is more stable when compared to a non-modified Catofin Cr/Al$_2$O$_3$ catalyst. Yet, the Manganese-modified Cr/Al$_2$O$_3$-Catofin catalyst shows a decrease from 61.7 to 50.6% within 100 min when employed at a reaction temperature of 690° C.; see Example 2.

Taken together, the process of the present invention allows the oxidative dehydrogenation (ODH) of a paraffinic lower hydrocarbon such as isobutane to the corresponding olefinic lower hydrocarbon isobutene. Simultaneously, the product stream comprises a synthesis gas (syngas) mixture with a near stoichiometric composition useful in carbonylation reactions, e.g. for producing dimethyl ether (DME).

The invention claimed is:

1. Process for converting a feedstream, said process comprising:
    contacting the feedstream comprising a paraffinic lower hydrocarbon and carbon dioxide with a reduced catalyst composition on an inert support,
    wherein said catalyst composition comprises 1-10 mass % reduced La (lanthanum) metal and 1-10 mass % reduced Mn (manganese) metal, to produce a product stream comprising an olefinic lower hydrocarbon and synthesis gas,
    wherein the paraffinic lower hydrocarbon to carbon dioxide ratio is in the range of about 0.7 to 1.

2. The process of claim 1, wherein said catalyst composition further comprises 0.3-3 mass % alkali metal (Group 1) as a promoter.

3. The process of claim 2, wherein said alkali metal is K (potassium) metal.

4. The process of claim 1, wherein said catalyst composition comprises 1-5 mass % reduced La (lanthanum) metal.

5. The process of claim 1, wherein said catalyst composition comprises 1-5 mass % reduced Mn (manganese) metal.

6. The process of claim 1, wherein said inert support is selected from the group consisting of alumina (Al$_2$O$_3$), silica (SiO$_2$), titania (TiO$_2$), zirconia (ZrO$_2$) and magnesia (MgO).

7. The process of claim 1, wherein said paraffinic lower hydrocarbon is isobutane and wherein said product stream comprises isobutene, propane and synthesis gas.

8. The process of claim 7, wherein the reaction temperature is from 670-710° C., the reaction pressure is from atmospheric to 0.5 MPa, and the space velocity is about 400-600 h$^{-1}$.

9. The process of claim 1, wherein said inert support is selected from the group consisting of alumina (Al$_2$O$_3$), silica (SiO$_2$), titania (TiO$_2$), zirconia (ZrO$_2$) and magnesia (MgO); and wherein the reaction temperature is from 670-710° C., the reaction pressure is from atmospheric to 0.5 MPa, and the space velocity is about 400-600 h$^{-1}$.

10. The process of claim 9, wherein said paraffinic lower hydrocarbon is isobutane and wherein said product stream comprises isobutene, propane and synthesis gas.

11. The process of claim 1, wherein said catalyst composition comprises 1-5 mass % reduced La (lanthanum) metal and 1-5 mass % reduced Mn (manganese) metal; and wherein said inert support is selected from the group consisting of alumina ($Al_2O_3$), silica ($SiO_2$), titania ($TiO_2$), zirconia ($ZrO_2$) and magnesia (MgO).

12. Process for converting a feedstream, said process comprising:

contacting the feedstream comprising a paraffinic lower hydrocarbon and carbon dioxide with a reduced catalyst composition on an inert support, to produce a product stream comprising an olefinic lower hydrocarbon and synthesis gas, wherein said catalyst composition comprises 1-10 mass % reduced La (lanthanum) metal and 1-10 mass % reduced Mn (manganese) metal, 0.3-3 mass % alkali metal (Group 1);

wherein said inert support is selected from the group consisting of alumina ($Al_2O_3$), silica ($SiO_2$), titania ($TiO_2$), zirconia ($ZrO_2$) and magnesia (MgO); and wherein the reaction temperature is from 670-710° C., the reaction pressure is from atmospheric to 0.5 MPa, the space velocity is about 400-600 $h^{-1}$, and the paraffinic lower hydrocarbon to CO2 ratio is in a range of about 0.7-1.

13. The process of claim 12, wherein said alkali metal is K (potassium) metal.

14. The process of claim 12, wherein said paraffinic lower hydrocarbon is isobutane and wherein said product stream comprises isobutene, propane and synthesis gas.

15. The process of claim 12, wherein said catalyst composition comprises 1-5 mass % reduced La (lanthanum) metal, 1-5 mass % reduced Mn (manganese) metal, 0.3-3 mass % K (potassium) metal.

16. The process of claim 1, wherein the synthesis gas has as $H_2$/CO ratio of 0.8 to 1.2.

17. The process of claim 12, wherein the synthesis gas has as $H_2$/CO ratio of 0.8 to 1.2.

\* \* \* \* \*